(12) United States Patent
Chang

(10) Patent No.: US 10,830,319 B2
(45) Date of Patent: Nov. 10, 2020

(54) TRANSMISSION STRUCTURE OF OZONE TESTING MACHINE

(71) Applicant: EKTRON TEK CO., LTD., Changhua County (TW)

(72) Inventor: Yau-Dong Chang, Changhua County (TW)

(73) Assignee: EKTRON TEK CO., LTD., Changhua County (TW)

( * ) Notice: Subject to any disclaimer, the term of this patent is extended or adjusted under 35 U.S.C. 154(b) by 135 days.

(21) Appl. No.: 16/243,912

(22) Filed: Jan. 9, 2019

(65) Prior Publication Data

US 2019/0360566 A1 Nov. 28, 2019

(30) Foreign Application Priority Data

May 24, 2018 (TW) .............................. 107206846 U

(51) Int. Cl.
*F16H 25/20* (2006.01)
*G01N 3/00* (2006.01)
*G01N 17/00* (2006.01)

(52) U.S. Cl.
CPC ........... *F16H 25/2015* (2013.01); *G01N 3/00* (2013.01); *G01N 17/00* (2013.01); *F16H 2025/204* (2013.01); *F16H 2025/2096* (2013.01)

(58) Field of Classification Search
CPC ....... F16H 2025/204; F16H 2025/2075; F16H 2025/2096; F16H 25/2015; F16H 37/16; G01N 2203/0066; G01N 2203/027; G01N 3/32; G01N 3/04; G01N 3/08; G01N 2203/0405; G01N 2203/0411; G01N 2203/0017; G01N 3/00; G01N 2203/0071; G01N 3/20; G01N 2203/0094; G01N 3/10; G01N 2203/0019; G01N 3/062; G01N 17/00; G01N 33/445; G01B 5/30; G01B 7/18; G01B 11/16; G01B 11/18; G01B 7/16; G01L 1/24
USPC ......... 73/799, 856, 857, 787, 788, 789, 795, 73/800; 33/787, 790
See application file for complete search history.

(56) References Cited

U.S. PATENT DOCUMENTS

| 4,574,642 | A | * | 3/1986 | Fleischman | ............... | G01N 3/32 73/799 |
| 4,690,001 | A | * | 9/1987 | Harvey | ..................... | G01D 5/34 348/294 |
| 5,291,279 | A | * | 3/1994 | Imao | ...................... | G01B 11/16 348/92 |

(Continued)

*Primary Examiner* — John Fitzgerald
*Assistant Examiner* — Truong D Phan

(57) ABSTRACT

A transmission structure of an ozone testing machine has: a transmission frame, a rotation unit, a connecting unit, and a lifting unit. The transmission structure is connected to the lifting shaft and the lifting device via the connecting unit, the bottom of the sleeve of the connecting unit is provided with threaded member screwed to the threaded rod of the lifting device, and the sleeve is fixed onto the sliding member to achieve the linear displacement along the guiding track. During the clockwise and reverse rotations of the servo motor of the lifting device, the lifting shaft can achieve the synchronous operation of the rotation and lifting due to the limited connection with the connecting unit, thereby greatly improving the smoothness of the test process, while maintaining the static and dynamic tests.

7 Claims, 9 Drawing Sheets

(56) References Cited

U.S. PATENT DOCUMENTS

| | | | | |
|---|---|---|---|---|
| 5,959,215 | A * | 9/1999 | Ono | G01N 3/36 |
| | | | | 73/789 |
| 9,528,945 | B2 * | 12/2016 | Handler | G01N 21/95 |
| 2003/0033896 | A1 * | 2/2003 | Borowczak | G01N 33/445 |
| | | | | 73/866 |
| 2012/0287248 | A1 * | 11/2012 | Erdman, III | G01N 3/068 |
| | | | | 348/47 |

\* cited by examiner

TRANSMISSION STRUCTURE OF OZONE TESTING MACHINE

BACKGROUND OF INVENTION

1. Field of Invention

The present invention relates to a testing machine, and more particularly to a transmission structure of an ozone testing machine.

2. Description of the Related Art

Currently, for testing rubber fatigue and aging, the test is carried out by using ultraviolet rays, ozone or stretching to achieve the rubber test object. When the above test is performed, the rubber test substances are clamped on the turntables in the test machine. In the above, the rotation is driven by the rotating mechanism, so that the test conditions of the respective objects in the detection space tend to be the same, and the static test purpose is achieved, because the rotation actuation and the stretching and extension operation are difficult to be synchronized on the same test machine. When the test object is subjected to a dynamic test of tensile elongation, it must be tested by another test machine having a lifting mechanism, and the stretching process of the lifting mechanism is not adjustable, so that the dynamic test cannot be observed while increasing the stretching length. The fatigue degree of the test object needs to be adjusted manually, and the test machine must be turned off before operation which is extremely inconvenient.

Therefore, it is desirable to provide a transmission structure of an ozone testing machine to mitigate and/or obviate the aforementioned problems.

SUMMARY OF THE INVENTION

An objective of present invention is to provide a transmission structure of an ozone testing machine has: a transmission frame, a rotation unit, a connecting unit, a lifting unit and a testing case. A transmission structure of an ozone testing machine has: a transmission frame, a rotation unit, a connecting unit, and a lifting unit. The transmission structure is connected to the lifting shaft and the lifting device via the connecting unit, the bottom of the sleeve of the connecting unit is provided with threaded member screwed to the threaded rod of the lifting device, and the sleeve is fixed onto the sliding member to achieve the linear displacement along the guiding track. During the clockwise and reverse rotations of the servo motor of the lifting device, the lifting shaft can achieve the synchronous operation of the rotation and lifting due to the limited connection with the connecting unit, thereby greatly improving the smoothness of the test process, while maintaining the static and dynamic tests.

Other objects, advantages, and novel features of invention will become more apparent from the following detailed description when taken in conjunction with the accompanying drawings.

DETAILED DESCRIPTION OF THE PREFERRED EMBODIMENT

Figure 1:
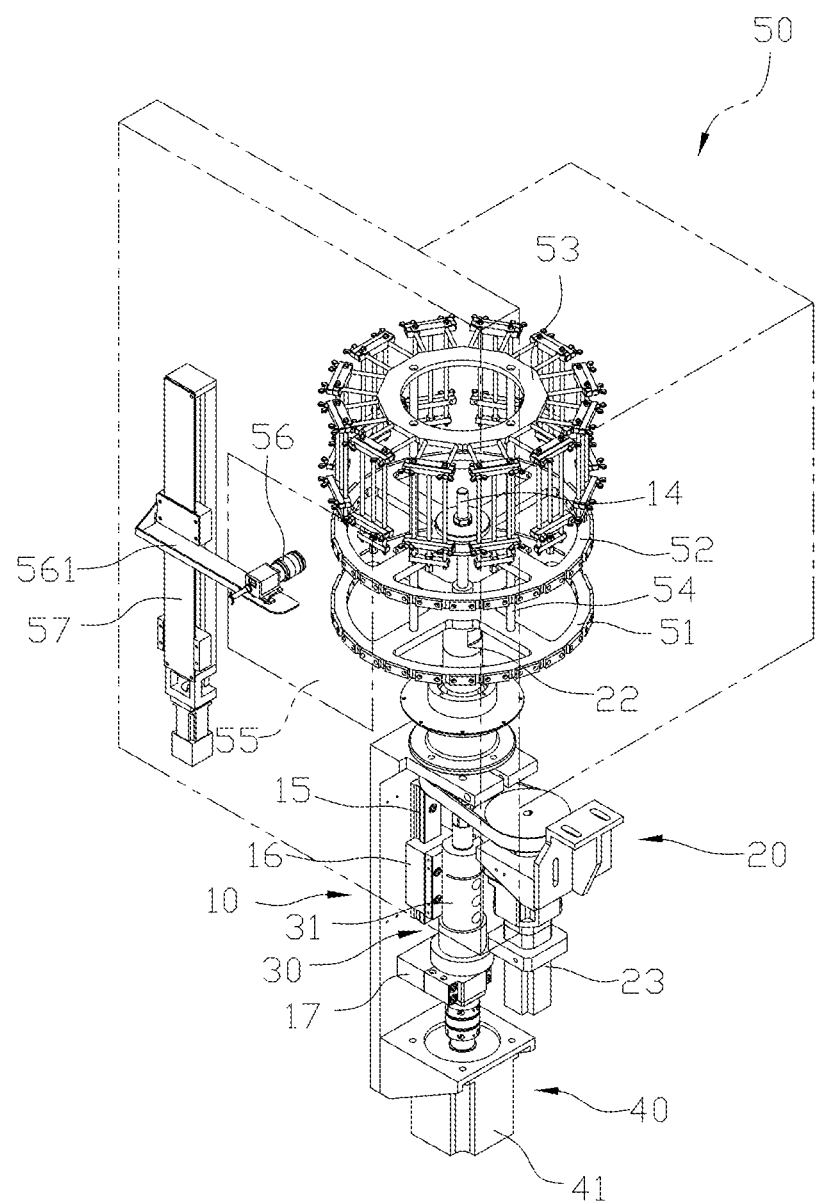
FIG. 1 is a perspective view of a preferred embodiment according to the present invention.
Figure 2:
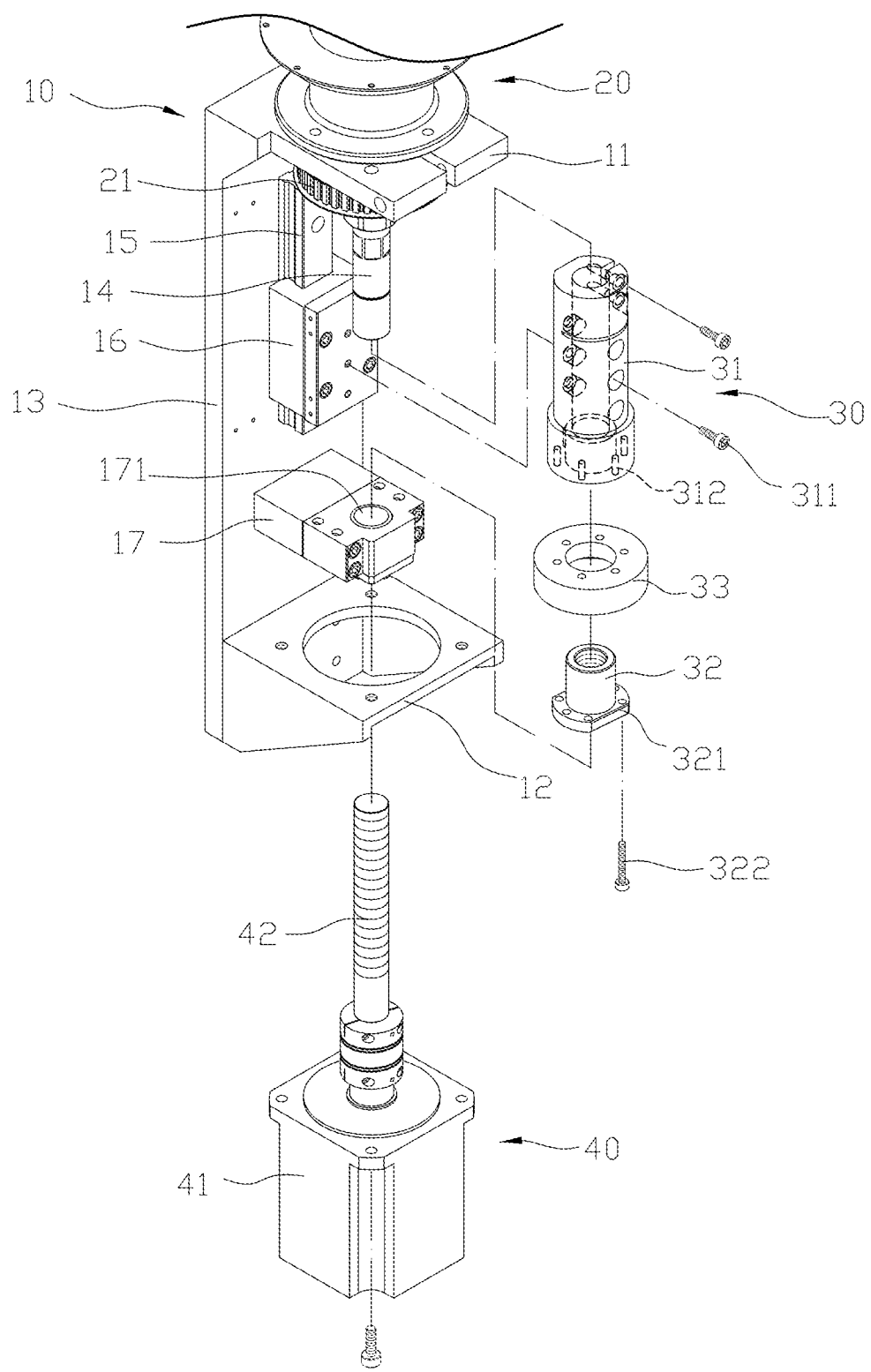
FIG. 2 is an exploded view of the preferred embodiment according to the present invention.
Figure 3:
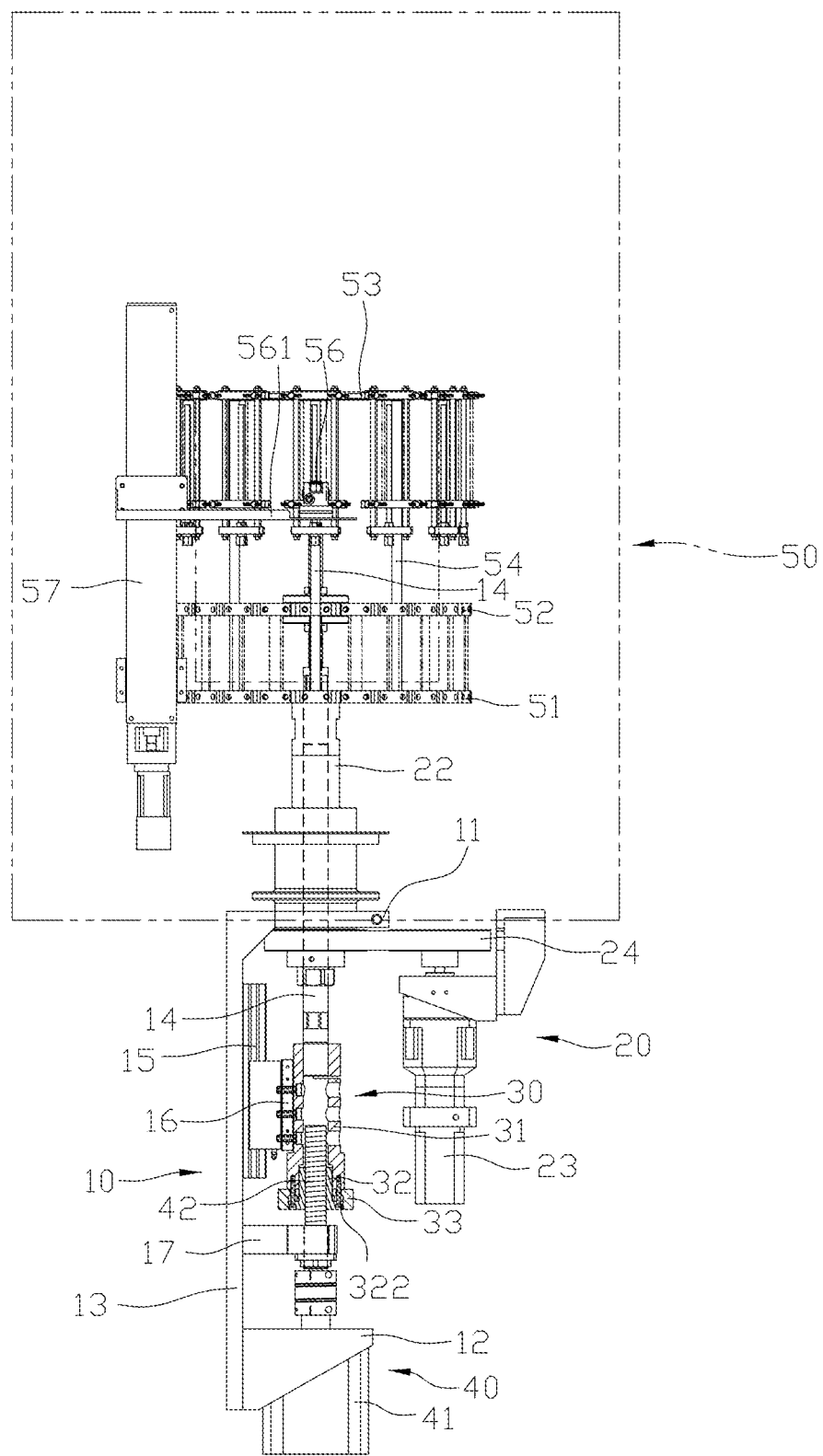
FIG. 3 is the front view of the preferred embodiment according to the present invention.
Figure 4:
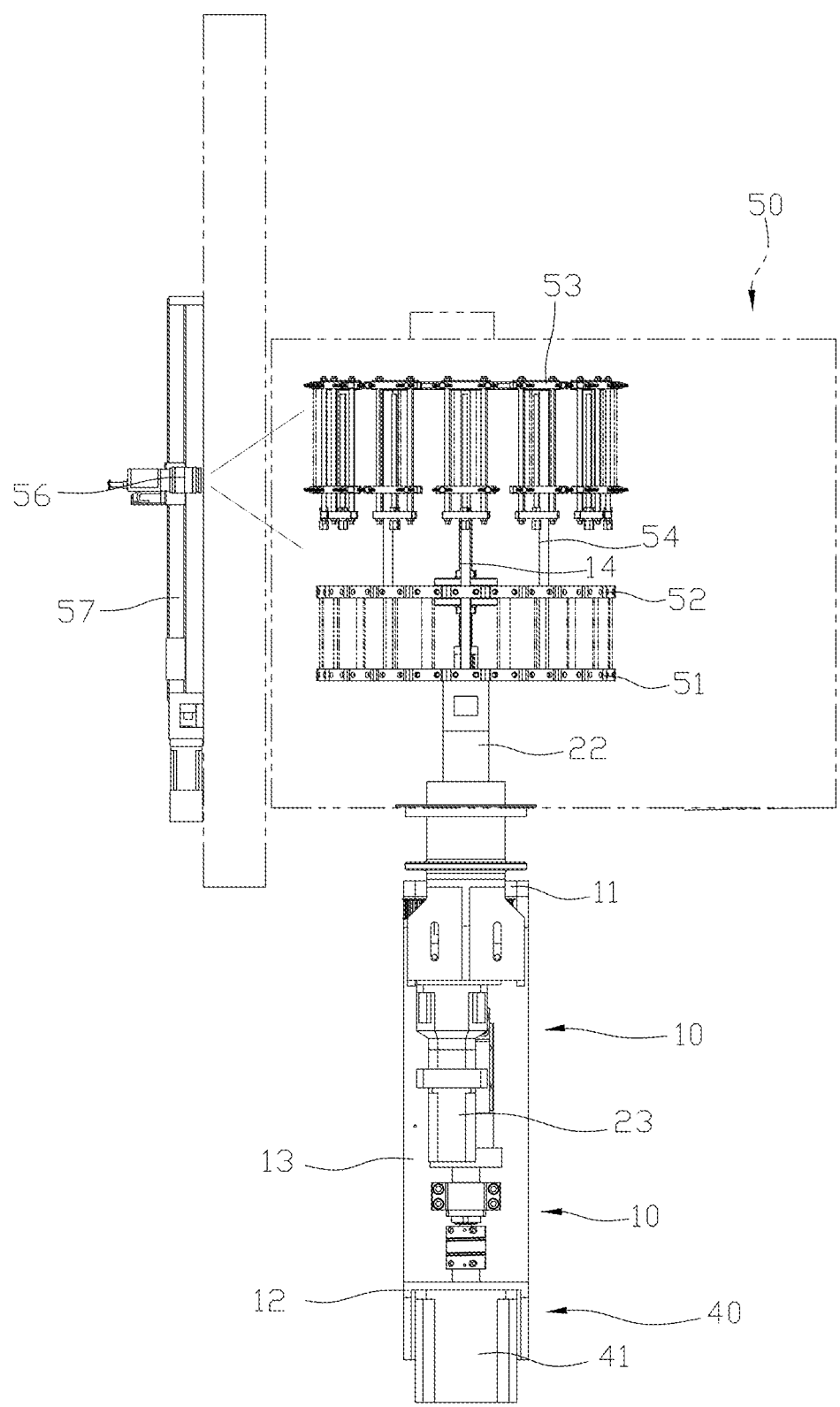
FIG. 4 is a side view of the preferred embodiment according to the present invention.

Please refer to FIGS. 1, 2, 3 and 4. A transmission structure of an ozone testing machine comprises: a transmission frame 10, a rotation unit 20, a connecting unit 30, a lifting unit 40 and a testing case 50. The transmission frame 10 has a top member 11 and a bottom member 12 parallel with each other, a side plate 13 connecting the top member 11 and the bottom member 12, and a lifting shaft 14 pivoted onto the top member 11. The side plate 13 has a guiding track 15 parallel to the lifting shaft 14 and provided with a sliding member 16. A positioning base 17 is mounted between the guiding track 15 and the bottom member 12, and the positioning base 17 further has an engaging aperture 171 facing the lifting shaft 14. The engaging aperture 171 is provided with a bearing (not shown). The rotation unit 20 has a belt wheel 21 and a rotating shaft 22 coupled with each other and both mounted onto the top member 11 of the transmission frame 10 via the lifting shaft 14 and a driving motor 23 connected to a belt 24 and the belt wheel 23 driving the rotating shaft 22. The rotating shaft 22 and the lifting shaft 14 are not connected, and both ends of the lifting shaft 14 extend out of the rotating shaft 22. The connecting unit 30 has a sleeve 31 and a threaded member 32. A top end of the sleeve 31 is jacked and secured onto the lifting shaft 14, a longitude side of the sleeve 31 is secured onto the sliding member 16 with a plurality of first locking members 311, to allow the sleeve 31 to move with the sliding member 16 along the guiding track 15 and drive the lifting shaft 14. The sleeve 31 is further provided with a plurality of locking apertures 312 at the bottom end, and a washer is placed adjacent to the bottom end. Furthermore, the threaded member 32 is placed through the washer 33 and enters into the sleeve 31. The threaded member further has a limiting plate 321 at a closed end, the limiting plate 321 pushes against the washer, and a plurality of second locking members 322 secure the limiting plate 321 and the washer 33 onto the locking apertures 312 of the sleeve 31. The lifting unit 40 has a servo motor 41 and a threaded rod 42 driven by the servo motor 41. The servo motor 41 is secured onto the bottom member 12 of the transmission frame 10, and the threaded rod 42 is placed through the positioning base 17 and engages with the threaded member 32 below the sleeve 31. Therefore, the rotation of the servo motor 41 drives the movement of the connecting unit 30. The testing case 50 has a first rotating disk 51, a second rotating disk 52 and a third rotating disk 53 connected via a plurality of connecting rods 54, such that the second rotating disk 52 is capable of moving between the first and third disks 51, 53. The first rotating disk 51 is mounted onto an upper end of the rotating shaft 22, and the lifting shaft 14 passes through the rotating shaft 22 to assemble with the second rotating disk 52. The testing case 50 has an observing window 55 provided with a camera 56 and a sliding track 57, and the camera 56 is attached onto a sliding member 561 which is movable along the sliding track 57.

As shown in FIGS. 1 to 4, in the structure of the transmission frame 10, the lifting shaft 14 is mounted by the top member 11, and the rotation unit 20 is pivoted to the lifting shaft 14. The lower end of the lifting shaft 14 protrudes from the belt wheel 21 and is sleeved with the sleeve 31 of the connecting unit 30. The sleeve 31 is fixed to the sliding member 16 with the locking members 311 on its side, and the sliding member 16 is slidably coupled to the guiding track 15, so that the sleeve 31 is driven by the sliding member 16 on the guiding track 15 with only linear movement. The servo motor 41 of the lifting unit 40 is mounted onto the bottom member 12 of the transmission frame 10, and the threaded rod 42 is placed through the bottom member 12 and the engaging aperture 171 of the positioning base 17 and then screwed to the threaded member 32 at the bottom of the sleeve 31 of the connecting unit 30. With the forward and reverse movement of the servo motor 41, the sleeve 31 is driven by the sliding member 16 to move up and down along the guiding track 15 to achieve the movements of the lifting shaft 14. The top member 11 of the transmission frame 10 is mounted at the bottom of the testing case 50, and the rotating shaft 22 of the rotation unit 20 is disposed in the testing case 50 and engaged with the first rotating disk 51. The upper end of the lifting shaft 14 protrudes outside of the rotating shaft 22 and extends upwardly to connect to the second rotating disk 52, and the first, second and third rotating disks 51, 52, 53 are connected with a plurality of links 54, such that the first, second and third rotating disks 51, 52, 53 have synchronized rotation states. The second rotating disk 52 is driven by the lifting shaft 14 to achieve a separate lifting movement.

Figure 5:
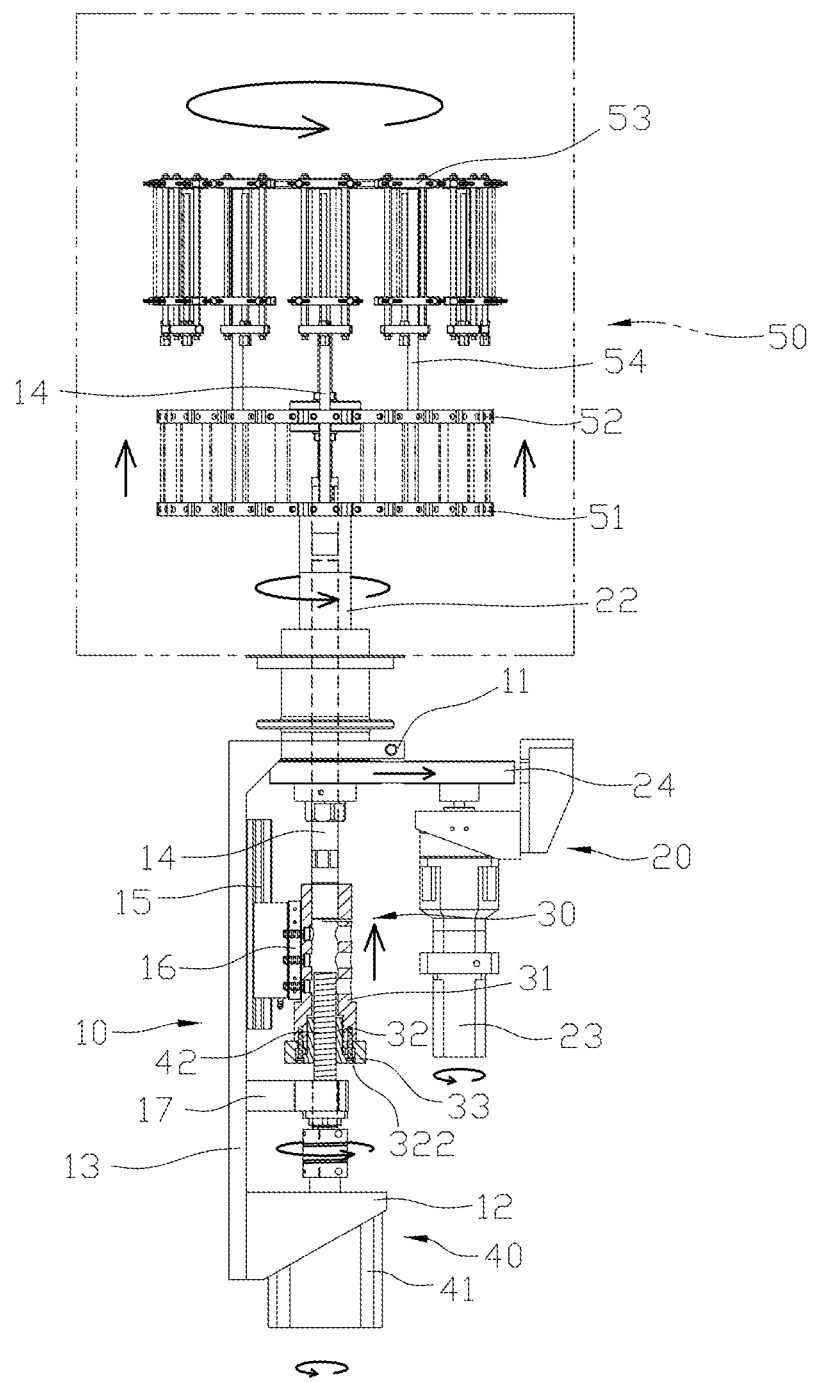
FIG. 5 is a schematic drawing of the rotation and ascent operations according to the preferred embodiment of the present invention.
Figure 6:
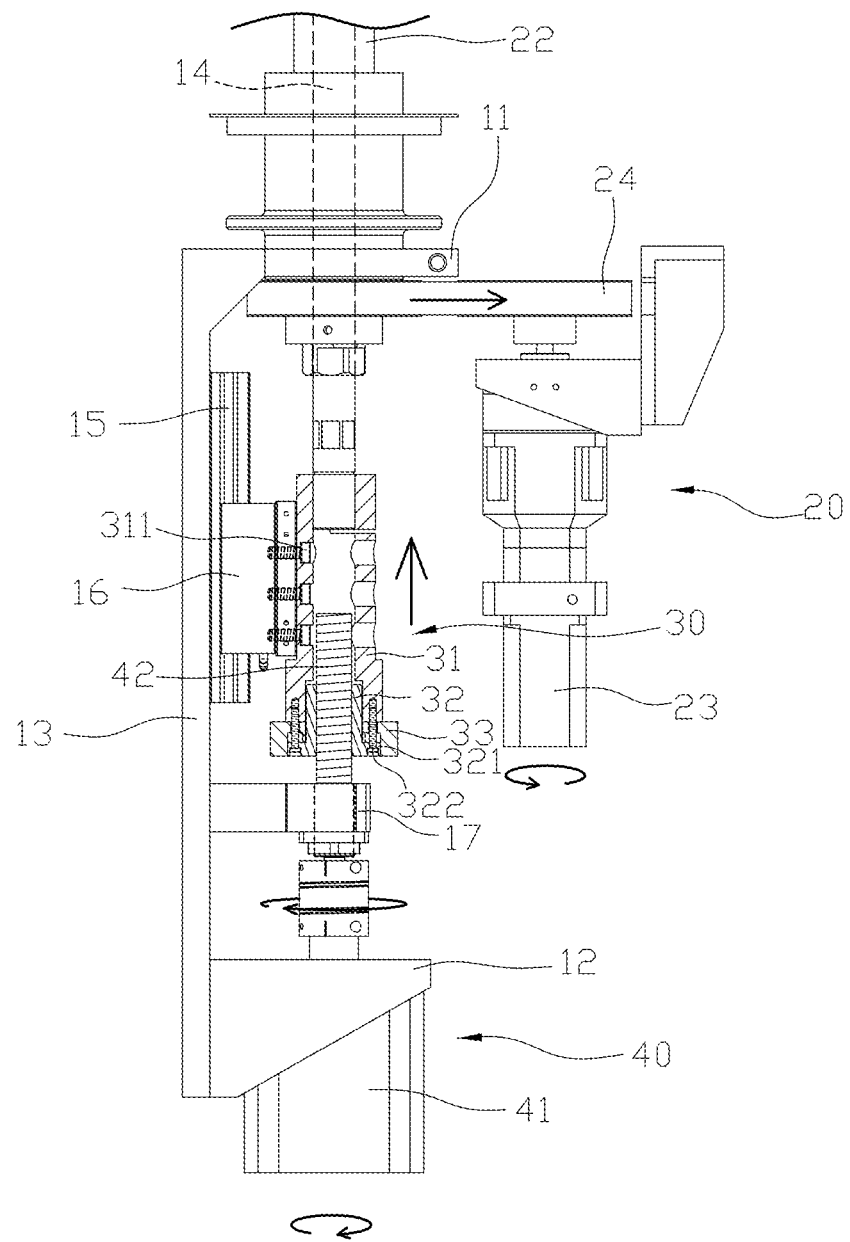
FIG. 6 is a schematic drawing of the lifting device driving the lifting rod to ascent according to the preferred embodiment of the present invention.
Figure 7:
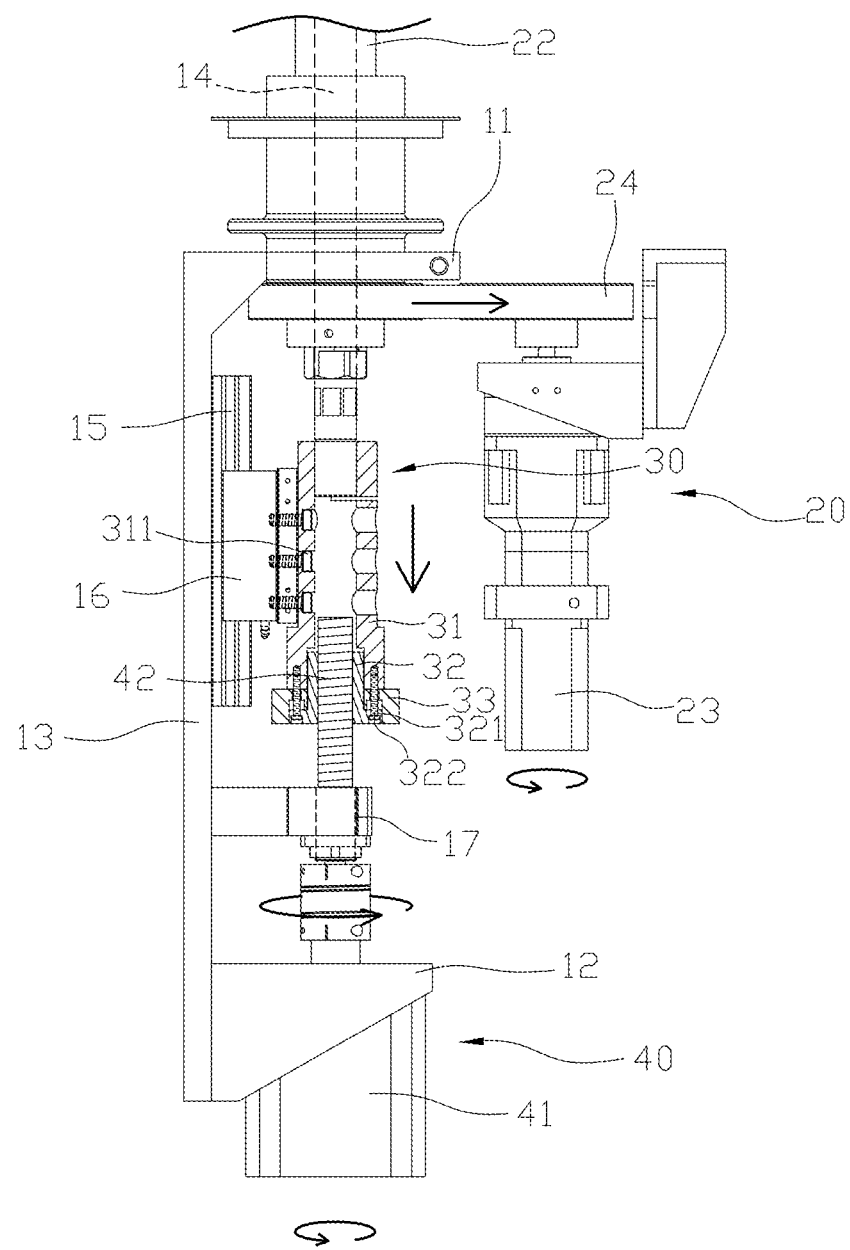
FIG. 7 is a schematic drawing of the lifting device driving the lifting rod to descend according to the preferred embodiment of the present invention.
Figure 8:
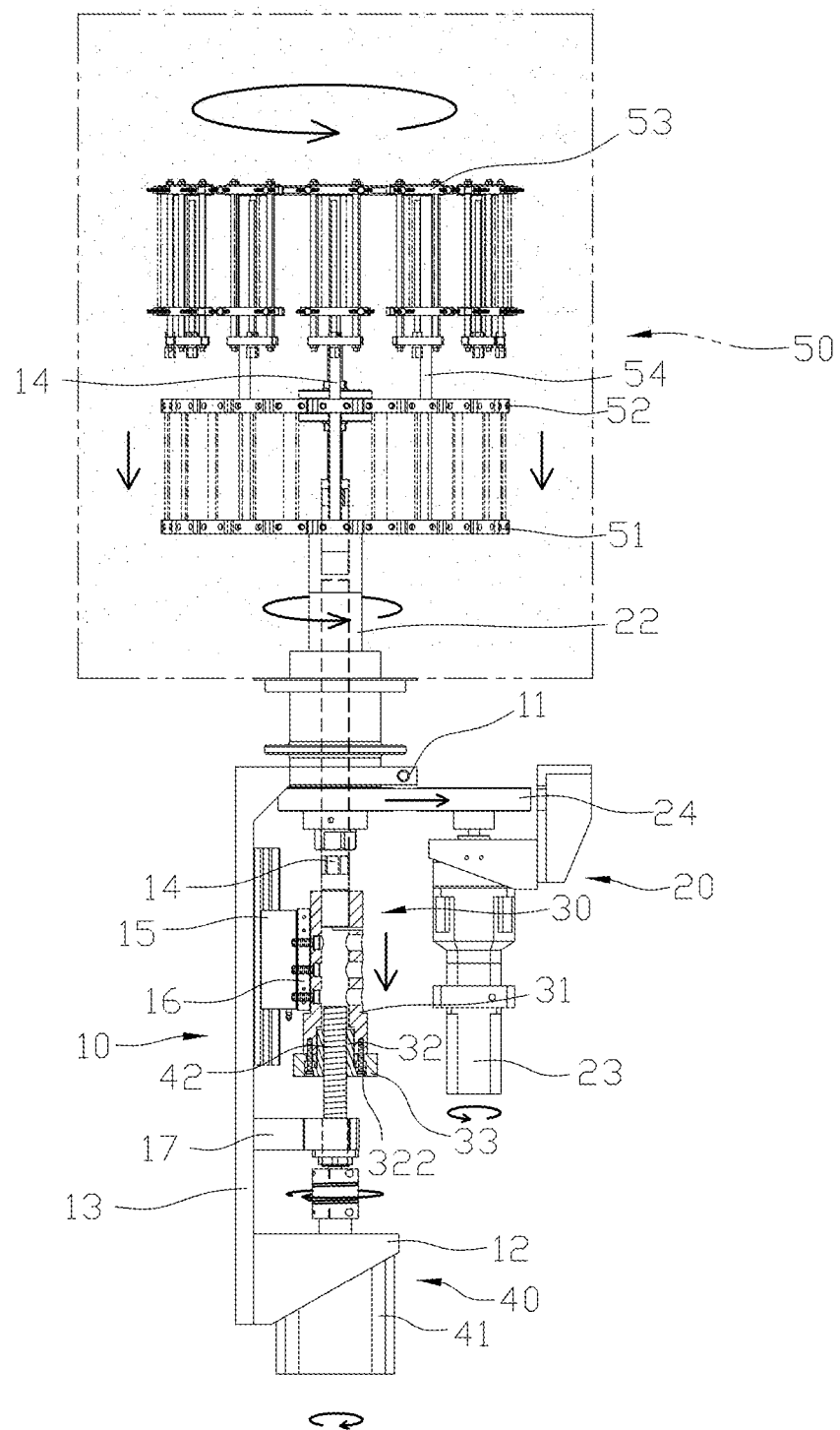
FIG. 8 is a schematic drawing of the rotation and descent movement according to the preferred embodiment of the present invention.
Figure 9:
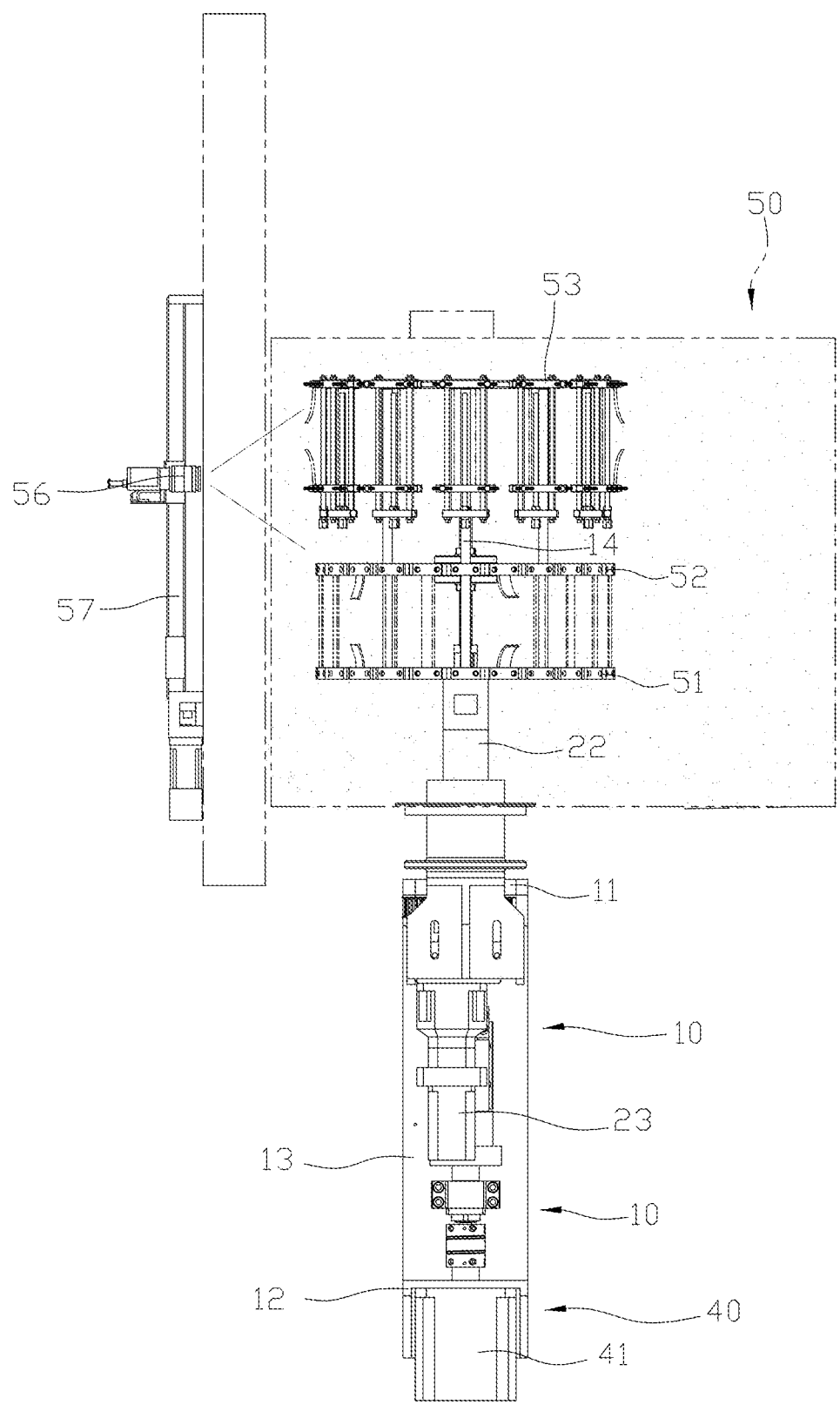
FIG. 9 is a schematic drawing showing the camera recording the testing process according to the preferred embodiment of the present invention.

For the actual use of the structure, please refer to FIG. 5 with FIGS. 6, 7, and 8. The ozone testing machine is used for testing fatigue and aging of cured films such as rubber, plastic, silicone, etc. The first and second rotating disks 51, 52 are provided with symmetrical clamps for clamping the film between on the first and second rotating disks 51, 52 for dynamic testing, and the third rotating disk 53 is provided with separate clamps for clamping the film for static test. During the actual testing of the ozone testing machine, the testing case 50 is filled with ozone gas internally, and the rotation unit 20 and the lifting unit 40 system can be activated synchronously. The rotation unit 20 is driven to rotate by the driving motor 23 moving the belt 23 to pull the belt wheel 21, so that the rotating shaft 22 rotates the first rotating disk 51 in order to rotate the first, second and third rotating disks 51, 52, 53 via the connection of the plurality of links 54 synchronously. The lifting unit 40 drives the threaded rod 42 forward and reverse through the servo motor 41, such that the sleeve 31 of the connecting unit 30 utilizes the threaded member 32 to rotate with the threaded rod 42. Since the sleeve 31 is limited onto the sliding member 16 and can only be driven along the threaded rod 42 and the guiding track 15, and then the lifting shaft 14 drives the second rotating disk 52 to move up and down. At the same time, the film clamped between the first and second rotating disks 51, 52 is pulled by the lifting movement of the second rotating disk 52, to achieve the dynamic test. Through the above test process, the static and dynamic tests for the film can be simultaneously achieved. Furthermore, the testing case 50 is further equipped with the camera 56, please also refer to FIG. 9, for observing and recording fatigue fractures during the dynamic test process, which can help to collect data and reduce labor costs.

With the structure of the above specific embodiment, the following benefits can be obtained: the transmission structure is connected to the lifting shaft 14 and the lifting device 40 via the connecting unit 30, the bottom of the sleeve 31 of the connecting unit 30 is provided with threaded member 32 screwed to the threaded rod 42 of the lifting device 40, and the sleeve 31 is fixed onto the sliding member 16 to achieve the linear displacement along the guiding track 15. During the clockwise and reverse rotations of the servo motor 41 of the lifting device 40, the lifting shaft 14 can achieve the synchronous operation of the rotation and lifting due to the limited connection with the connecting unit 30, thereby greatly improving the smoothness of the test process, while maintaining the static and dynamic tests.

The lifting device 40 utilizes the servo motor 41 to drive the threaded rod 42 to achieve the lifting operation, which can be operated and controlled by a computer and can be adjusted at any time. Thereby, it improves the convenience of structural operation adjustment and effectively reducing the labor cost. The fatigue fracture of the film can also observe through the adjustment of the stretching process, which increases the accuracy of the dynamic testing.

Although the present invention has been explained in relation to its preferred embodiment, it is to be understood that many other possible modifications and variations can be made without departing from the spirit and scope of invention as hereinafter claimed.

What is claimed is:

1. A transmission structure of an ozone testing machine comprising:
    a transmission frame mounted at a bottom portion of the ozone testing machine, the transmission frame having a top member and a bottom member parallel with each other, a side plate connecting the top member and the bottom member; a lifting shaft pivoted onto the top member; the side plate having a guiding track parallel to the lifting shaft and provided with a sliding member; a positioning base mounted between the guiding track and the bottom member, the positioning base further having an engaging aperture facing the lifting shaft;
    a connecting unit having a sleeve and a threaded member, a top end of the sleeve jacked and secured onto the lifting shaft, a longitude side of the sleeve secured onto the sliding member with a plurality of first locking members, to allow the sleeve to move with the sliding member along the guiding track and drive the lifting shaft; a bottom end of the sleeve jacked with the threaded member; the threaded member having a limiting plate at a closed end, the limiting plate secured onto the bottom end of the sleeve with a plurality of second locking members; and
    a lifting unit having a servo motor and a threaded rod driven by the servo motor, the servo motor secured onto the bottom member of the transmission frame, the threaded rod placed through the positioning base and engaging with the threaded member below the sleeve.

2. The transmission structure of an ozone testing machine as claimed in claim 1, wherein the sleeve is further provided with a plurality of locking apertures at the bottom end, a washer is placed adjacent to the bottom end, the threaded member is placed through the washer and enters into the sleeve, the limiting plate of the threaded member pushes against the washer, and the plurality of second locking members secure the limiting plate and the washer onto the locking apertures of the sleeve.

3. The transmission structure of an ozone testing machine as claimed in claim 1, wherein the transmission frame is further provided with a bearing in the engaging aperture of the positioning base.

4. The transmission structure of an ozone testing machine as claimed in claim 1 further comprising: a rotation unit having a belt wheel and a rotating shaft coupled with each other and both mounted onto the top member of the transmission frame via the lifting shaft, and a driving motor connected to a belt and the belt wheel driving the rotating shaft.

5. The transmission structure of an ozone testing machine as claimed in claim 4 further comprising: a testing case having a first rotating disk, a second rotating disk and a third rotating disk connected via a plurality of connecting rods, such that the second rotating disk is capable of moving between the first and third disks; the first rotating disk is mounted onto an upper end of the rotating shaft, and the lifting shaft passes through the rotating shaft to assemble with the second rotating disk.

6. The transmission structure of an ozone testing machine as claimed in claim 5, wherein the testing case has an observing window provided with a camera.

7. The transmission structure of an ozone testing machine as claimed in claim 6, wherein the testing case further has a sliding track, and the camera is attached onto a sliding member which is movable along the sliding track.

\* \* \* \* \*